(12) United States Patent
Forber

(10) Patent No.: US 6,589,256 B2
(45) Date of Patent: Jul. 8, 2003

(54) COVERED SELF-EXPANDING VASCULAR OCCLUSION DEVICE

(75) Inventor: Simon J. Forber, Yversay (FR)

(73) Assignee: B. Braun Medical SAS (FR)

( * ) Notice: Subject to any disclaimer, the term of this patent is extended or adjusted under 35 U.S.C. 154(b) by 327 days.

(21) Appl. No.: 09/781,702

(22) Filed: Feb. 13, 2001

(65) Prior Publication Data

US 2001/0012949 A1 Aug. 9, 2001

Related U.S. Application Data

(60) Division of application No. 09/314,237, filed on May 18, 1999, now Pat. No. 6,221,086, which is a continuation-in-part of application No. 09/042,108, filed on Mar. 13, 1998, now Pat. No. 5,925,060.

(51) Int. Cl.[7] .............................................. A61B 17/08
(52) U.S. Cl. ...................................... 606/151; 606/157
(58) Field of Search ................................ 606/151, 157, 606/191, 198, 195, 200, 127

(56) References Cited

U.S. PATENT DOCUMENTS

| | | |
|---|---|---|
| 4,994,069 A | 2/1991 | Ritchart et al. |
| 5,226,911 A | 7/1993 | Chee et al. |
| 5,423,849 A | 6/1995 | Engelson et al. |
| 5,522,822 A | 6/1996 | Phelps et al. |
| 5,733,294 A * | 3/1998 | Forber et al. ............... 606/151 |
| 5,776,140 A * | 7/1998 | Cottone ...................... 606/198 |
| 5,925,060 A * | 7/1999 | Forber ........................ 606/191 |
| 6,014,589 A * | 1/2000 | Farley et al. ................. 607/98 |

FOREIGN PATENT DOCUMENTS

| | | |
|---|---|---|
| DE | 92 05 797 | 6/1992 |
| FR | 2 645 028 A | 10/1990 |
| WO | 96/01591 | 1/1996 |
| WO | 97/27893 | 8/1997 |
| WO | 97/31672 | 9/1997 |

* cited by examiner

Primary Examiner—Kevin T. Truong
(74) Attorney, Agent, or Firm—Skinner and Associates

(57) ABSTRACT

A covered self-expanding vascular occlusion device and a method of making and using the device. The device comprises a braided wire member with at least two axially spaced securing members affixed to the braided wire member and a thin film covering at least half of the device. The braided member can be moved between a larger diameter ball-like shape or conical shape in its relaxed position, and a smaller diameter cylindrical shape in its stretched position. The film covering is applied to the device by first stretching a portion of film to form a shape similar to a portion of a device to be covered by the film, then inserting the device into the shape formed in the film so that the film covers at least half of the device, and trimming the film to separate the covered device from the remaining film. The device is used by installing it on the end of a tubular introducer where it is held in its relaxed position until needed. A sliding member inside of the introducer tube then pulls the device into the tube, moving the device to its stretched position as it does so. The sliding member is pulled out of the tube, releasing the device and leaving it inside of the tube and in its stretched condition. The tube is installed in a catheter, and the device pushed from the tube into, through, and out of the catheter where upon exiting the catheter the device then opens to its relaxed condition, lodges in the blood vessel, and immediately and completely occludes the vessel.

5 Claims, 8 Drawing Sheets

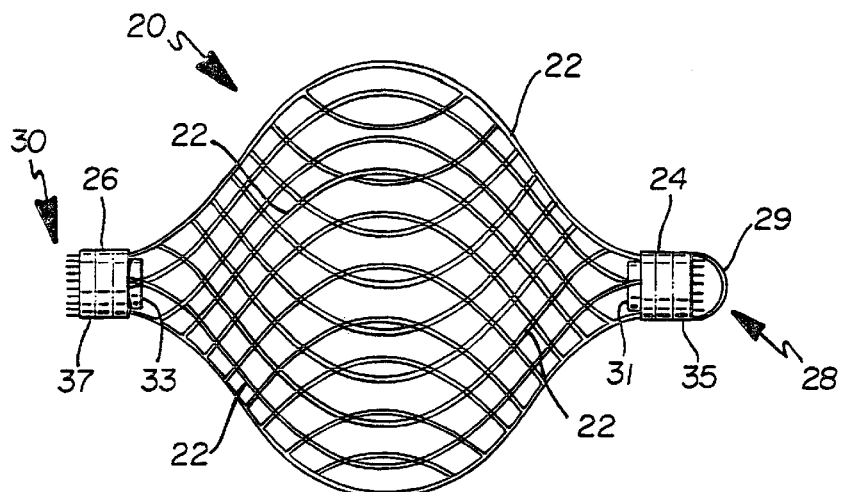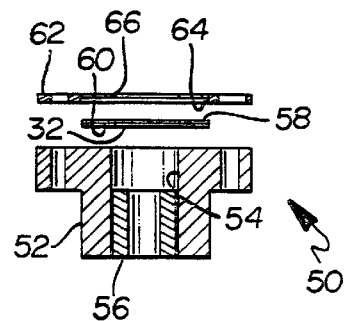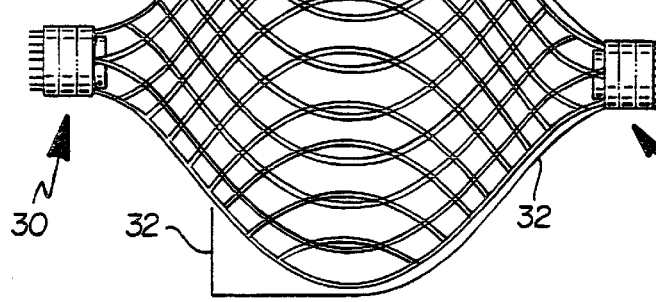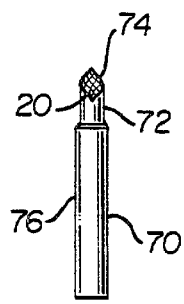
Fig. 1
Fig. 3
Fig. 2
Fig. 4

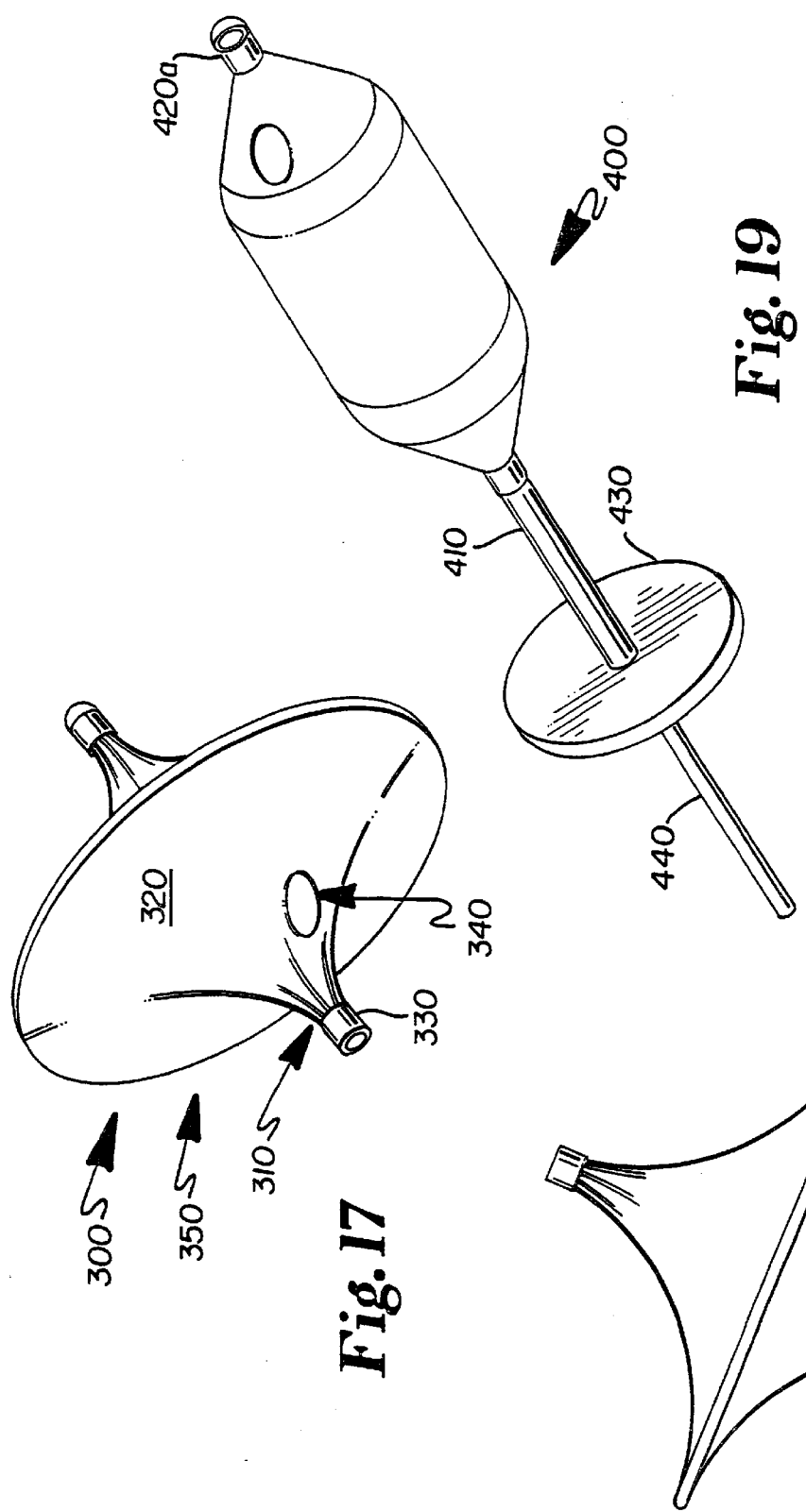

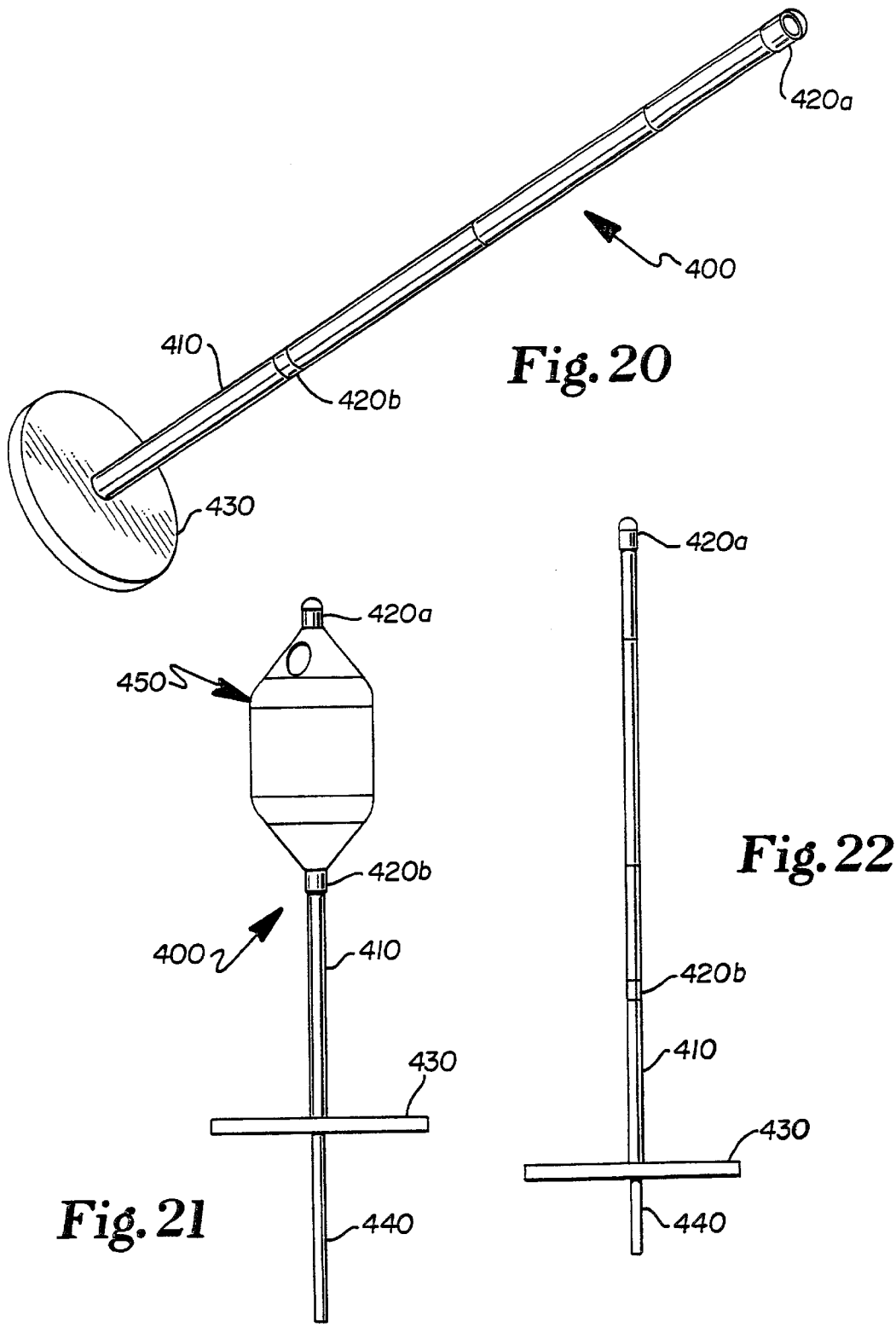

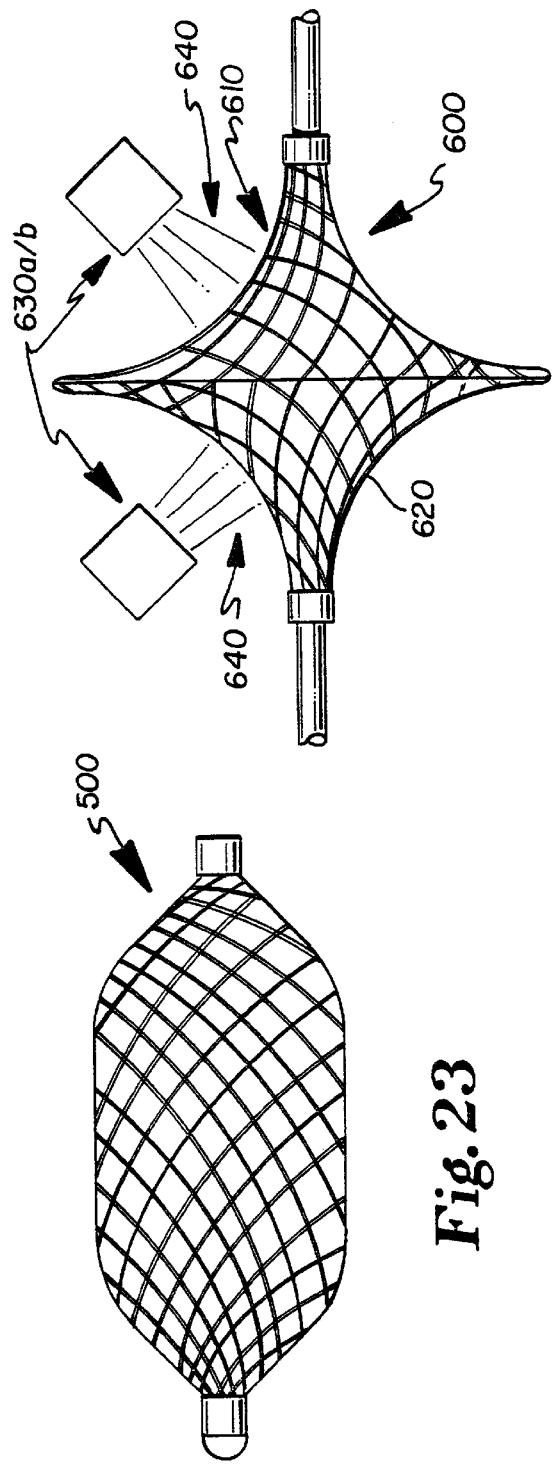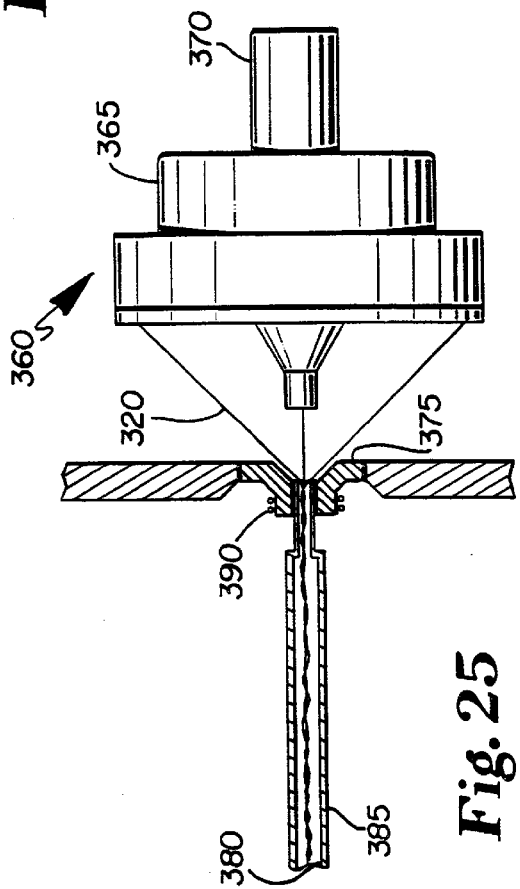

COVERED SELF-EXPANDING VASCULAR OCCLUSION DEVICE

CROSS-REFERENCE TO RELATED APPLICATIONS, IF ANY

This application is a division of application Ser. No. 09/314,237, filed May 18, 1999, now U.S. Pat. No. 6,221,086.

This is a continuation-in-part of U.S. patent application Ser. No. 09/042,108, filed Mar. 13, 1998, now U.S. Pat. No. 5,925,060 entitled Covered Self-Expanding Vascular Occlusion Device, pending, and which is hereby incorporated by reference.

STATEMENT REGARDING FEDERALLY SPONSORED RESEARCH OR DEVELOPMENT

Not applicable.

REFERENCE TO A MICROFICHE APPENDIX IF ANY

Not applicable.

BACKGROUND OF THE INVENTION

1. Field of the Invention

The present invention relates, generally to medical devices. More particularly, the invention relates to vasoocclusion devices used in radiology and embolotherapy.

2. Background Information

In embolotherapy, it is often desirable to occlude blood flow in a section of vasculature for purposes such as controlling internal bleeding, stopping blood supply to tumors, and relieving vessel-wall pressure in a region of a vessel aneurysm. Numerous devices have been developed for this purpose. U.S. Pat. No. 4,994,069 describes devices and methods such as cross-linking liquids, cyanoacrylate resins, balloons and helical wire coils. Helical coils found favor, but because they are dimensioned to engage the walls of the vessel, they are relatively stiff and difficult to advance through a catheter.

The device of U.S. Pat. No. 4,994,069 provides a smaller coiled wire that, when tensioned, would have a linear configuration allowing it to easily be advanced through a catheter to the desired site. When the wire exits the catheter, it relaxes and takes a random convoluted shape to form a space-filling mass lodged in the vessel at the site of release. However, because the final shape of the relaxed coil in the blood vessel is random, the precise location and specific length the device occupies in the vessel cannot be guaranteed.

Another problem with wire coils is providing enough occlusion to allow a blood clot to form. A partial solution is to coat the wire with fibers such as dacron or cotton, but recanalization can occur by resorption of the clot by the bodies fibrinolytic system. The fiber coating also increases the friction between the coated wire and the catheter making it more difficult to advance the coils through the catheter. Another way to combine fibers and coiled wire is disclosed in U.S. Pat. No. 5,226,911 where flexible fiber loops extend outward from windings of the coil at regular intervals.

An alternative to helical wire coils is tubular braided devices made from radiopaque fibers or wires as disclosed in U.S. Pat. No. 5,423,849. These braided structures are significantly smaller than the vessel into which they are to be introduced, so they could easily be pushed through a catheter. The tubular structure could be straight, or convoluted into a variety of shapes such as a circle, a "C" or a figure "8". Topically a plurality of devices are introduced at a site in the vasculature. The braided wires may have additional fibrous elements attached to them to increase the occludability of the device.

Another braided structure is disclosed in U.S. patent application Ser. No. 08/608,110, titled Self Expanding Vascular Occlusion Device, filed on Feb. 28, 1996. A braided tubular structure is compressed axially, which expands it diametrically. The structure is then heat-set in that shape. In one embodiment, the expanded portion is heat-set in the form of a disk. In another embodiment the device has two sections, each forming a disk which is then shaped into a cone, the final heat-set shape being similar to two cones attached end to end. One of these devices is straightened to its cylindrical braided form to advance it through a catheter. When it exits the catheter, the device returns to its formed shape and lodges in the blood vessel. Additional fibrous material may be attached inside the core of the device to improve its occludability.

Vascular occlusion with all of these devices depends on the flow of blood being restricted enough by the presence of a large quantity of fibrous material in the blood stream. Initial deployment of such devices significantly reduces blood flow, but flow may not completely stop it. Clots soon form in the deployed device or devices which further reduce blood flow. Blood flow eventually may be completely stopped by the device. This takes time. The effectiveness of such occlusion may also be quite variable. It is desirable An alternative to helical wire coils is tubular braided devices made from radiopaque fibers or wires as disclosed in U.S. Pat. No. 5,423,849. These braided structures are significantly smaller than the vessel into which they are to be introduced, so they could easily be pushed through a catheter. The tubular structure could be straight, or convoluted into a variety of shapes such as a circle, a "C" or a figure "8". Typically a plurality of devices are introduced at a site in the vasculature. The braided wires may have additional fibrous elements attached to them to increase the occludability of the device.

Another braided structure is disclosed in U.S. patent application Ser. No. 08/608,110, titled Self Expanding Vascular Occlusion Device, filed on Feb. 28, 1996. A braided tubular structure is compressed axially, which expands it diametrically. The structure is then heat-set in that shape. In one embodiment, the expanded portion is heat-set in the form of a disk. In another embodiment the device has two sections, each forming a disk which is then shaped into a cone, the final heat-set shape being similar to two cones attached end to end. One of these devices is straightened to its cylindrical braided form to advance it through a catheter. When it exits the catheter, the device returns to its formed shape and lodges in the blood vessel. Additional fibrous material may be attached inside the core of the device to improve its occludability.

Vascular occlusion with all of these devices depends on the flow of blood being restricted enough by the presence of a large quantity of fibrous material in the blood stream. Initial deployment of such devices significantly reduces blood flow, but flow may not completely stop. Clots soon form in the deployed device or devices which further reduce blood flow. Blood flow eventually may be completely stopped by the device. This takes time. The effectiveness of such occlusion may also be quite variable. It is desirable for a vascular occlusion device to be self-expanding, accurately positionable, and to completely occlude a blood vessel immediately upon deployment.

Despite the need in the art for a vascular occlusion device which overcomes the disadvantages, shortcomings and limitations of the prior art, none insofar as is known has been developed.

BRIEF SUMMARY OF THE INVENTION

A covered self-expanding vascular occlusion device comprises a braided wire member with at least two axially spaced securing members affixed to the braided wire member and a thin film covering at least half of the device. Moving the securing members axially relative to each other moves the braided wire member to shape a portion of the braided wire member intermediate the first and second securing members. The device is movable between a first stretched position in which the braided wire portion extends in an essentially cylindrical configuration to a maximum axial length and a minimum diameter, and a second relaxed position in which the axial length of the braided wire portion is reduced and its diameter is increased. In the relaxed position, the braided wire portion has a ball-like shape.

The film covering is applied to the device by first stretching a portion of film to form a shape similar to a portion of a device to be covered by the film, then inserting the device into the shape formed in the film so that the film covers at least half of the device, and trimming the film to separate the covered device from the remaining film. Stretching of the film is preferably accomplished by inserting a pin having a tip shaped similar to that of the device into a portion of film held in a fixture. The pin is withdrawn from the stretched film, the device is mounted on the end of a mandrel, and inserted into the stretched film. The film is made tight on the device preferably by further stretching of the film. After the film is trimmed, the covered device is removed from the mandrel.

The device is used by installing it on the end of a tubular introducer where it is held in its relaxed position until needed. A sliding member inside of the introducer tube then pulls the device into the tube, moving the device to its stretched position as it does so. The sliding member is pulled out of the tube, releasing the device and leaving it inside of the tube and in its stretched condition. The tube is installed in a catheter and the device pushed from the tube into, through, and out of the catheter where upon exiting the catheter the device then opens to its relaxed condition, lodges in the blood vessel, and immediately and completely occludes the vessel.

Alternative embodiments of the vascular occlusion device of the present invention include features for (1) melting film to wires to prevent film migration distally upon implantation, (2) providing holes in film to permit the device to open faster and to remain in place, (3) urinary incontinence treatment, (4) alternative expanded forms, and (5) film creation processes.

Accordingly, it is an object of the present invention to provide a self-expanding vascular occlusion device which can completely occlude a blood vessel immediately upon deployment. The features, benefits and objects of this invention will become clear to those skilled in the art by reference to the following description, claims and drawings.

BRIEF DESCRIPTION OF THE DRAWINGS

FIG. 1 is a side view of a ball-like shaped self-expanding vascular occlusion device without a film covering.

FIG. 2 is the device of FIG. 1 with a film covering.

FIG. 3 is a cross sectional partially exploded view of a holding fixture for stretching film to be applied to a vascular occlusion device.

FIG. 4 is a side view of a pin used to stretch film.

FIG. 17 is a perspective view of an alternative embodiment of the vascular occlusion device of the present invention.

FIG. 18 is a side view of the vascular occlusion device shown in FIG. 17.

FIG. 19 is a perspective view of an alternative embodiment of the vascular occlusion device of the present invention, in an expanded state, for use in treating urinary incontinence.

FIG. 20 is a perspective view of the vascular occlusion device shown in FIG. 19, in an unexpanded state.

FIG. 21 is a side view of the vascular occlusion device shown in FIG. 19.

FIG. 22 is a side view of the vascular occlusion device shown in FIG. 20.

FIG. 23 is an illustration of an alternative embodiment of the vascular occlusion device of the present invention.

FIG. 24 illustrates a method of making an alternative embodiment of the vascular occlusion device of the present invention.

FIG. 25 illustrates a method of melting the film at the proximal end of the device shown in FIGS. 17 and 18.

DETAILED DESCRIPTION

Figure 5:
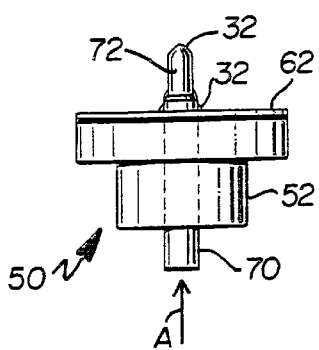
FIG. 5 is a side view showing the pin of FIG. 4 inserted into the holding fixture of FIG. 3 to stretch film.

The present invention is an improvement of the inventor's self-expanding vascular occlusion device disclosed in U.S. patent application Ser. No. 08/608,110 (the '110 application), titled Self Expanding Vascular Occlusion Device, filed on Feb. 28, 1996. The above patent application is hereby incorporated be reference.

Referring to FIGS. 1 and 2, a self-expanding vascular occlusion device 40 of the present invention is similar to the devices disclosed in the '110 application in that a ball-shaped structure 20 is formed by first braiding a plurality of wires 22 into a tubular structure and capturing the wires 22 in bands 24 and 26 located at a first end 28 and second end 30 of structure 20. As disclosed in the '110 application, bands 24 and 26 preferably capture wires 22 between inner band members 31 and 33 and outer band members 35 and 37, the outer band members 35 and 37 being crimped, welded, bonded, or otherwise attached to the inner band members 31 and 33 when wires 22 are in place. With wires 22 secured to bands 24 and 26, bands 24 and 26 are pushed axially toward each other, thereby causing the center of the braided tubular structure to expand diametrically to form a ball-like shape as shown in FIG. 1. Wires 22 are heat-set in this shape so that structure 20 retains its ball-like shape in when the force pushing bands 24 and 26 toward each other is removed. A smooth hemispherical cap 29 is formed on one end 28, preferably by capping end 28 with epoxy or other appropriate material.

If bands 24 and 26 were pushed further together, the structure 20 would form a single disk-like shape similar to the disk-like shape disclosed in the '110 application. If a single disk shaped device were to cant in the blood vessel so that the plane of the disk is no longer normal to the axis of the blood vessel, a significant portion of the edge of the disk will no longer be in contact with the wall of the blood vessel, thereby allowing leakage past the device. The ball-like shape offers an advantage over a single disk in that the ball-like shape may cant off the axis of the blood vessel and the outside of the ball-like shape will remain in contact with the vessel wall.

Wires 22 of the ball-like structure 20 are spaced relatively far apart in the expanded region of the structure, and alone may not provide adequate occlusion. The present invention applies a thin plastic film 32 over a major portion of the ball-like structure 20 to make the covered vascular occlusion device 40 of FIG. 2. Film 32 is stretched to form a shape similar to that of approximately half of the ball-like structure 20 as indicated by area 34. The structure 20 is inserted into the preshaped film and film 32 is further stretched so that film 32 covers end 28 and the film 32 follows the contour of structure 20 over area 34. Film 32 is trimmed to leave a cylindrical skirt section 36 extending from the major diameter of the structure 20 toward end 30. The final thickness of film 32 can be from five to fifteen micrometers, depending on the initial film thickness, which is approximately twice that of the final thickness. This extremely thin final film thickness is necessary for introducing the device through a catheter. When the covered device 40 is stretched for introduction through a catheter, the film 32 collapses and folds on itself as the diameter of the device 40 decreases. If the film 32 were much thicker, the collapsed film would take up too much space which may make the device fit too tightly in the catheter. When device 40 is deployed in a blood vessel, it opens upon exiting the catheter, thereby expanding the film again and completely occluding the vessel immediately upon opening.

Referring to FIGS. 3–12, the preferred method for forming the plastic film 32 and installing it onto a ball-shaped self-expanding vascular occlusion device is illustrated. The cross section of a cylindrical holding fixture 50 for stretching the film 32 is illustrated in FIG. 3. The holding fixture comprises a cylindrical body 52 having a bore 54 which holds a bushing 56. Bushing 56 guides mandrels used to stretch film 32 and install device 20 in the stretched film 32. Flat film 32, preferably low density polyethylene, is sandwiched between two rings 58 and 60, which are preferably made of PETG. Rings 58 and 60 trap film 32 and hold it taught. Rings 58 and 60 with film 32 are located on top of body 52 and secured with cover 62 which attaches to body 52. Cover 62 has a large diameter bore which receives rings 58 and 60, and a small diameter bore 66 above bore 64 which provides the proper diameter for film 32 to be stretched through it.

Referring to FIG. 4, a pin 70 has an upper portion 72 which has an outer diameter matching that of the outer diameter of the ball-shaped vascular occlusion device 20. End 74 of upper portion 72 is contoured to correspond to the contour of device 20. Device 20 is shown superimposed on end 74 of pin 70 to illustrate how the contours align. Lower portion 76 has an outer diameter that will allow it to align accurately and slide smoothly in bushing 56.

Referring to FIG. 5, pin 70 is inserted in bushing 56 of holding fixture 50 and pushed upward as indicated by arrow A so that upper portion 72 is pushed into film 32 thereby stretching film 32 to the form of upper portion 72. The step could also be accomplished by holding the pin 70 stationary and pushing the holding fixture 50 down onto the upper portion 72 of pin 70. It is also possible that the bushing 56 could be eliminated by using accurately indexable machines to hold pin 70 and film 32 and bring the two together.

Figure 6:
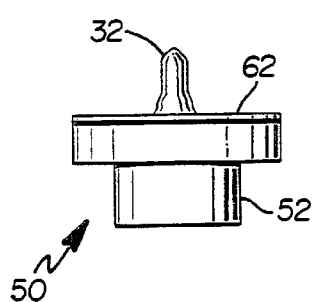
FIG. 6 is a side view of the holding fixture of FIG. 5 with the stretched film after the pin has been removed.

Referring to FIG. 6, once film 32 is stretched, pin 70 is withdrawn downward from holding fixture 50. This process inverts film 32 as pin 70 is withdrawn, so pressurized air is blown into holding fixture 50 to reinvert the film back to its stretched form as illustrated.

Figure 7:
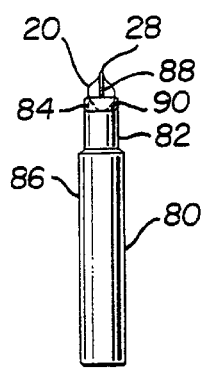
FIG. 7 is a side view of the vascular occlusion device of FIG. 1 attached to the top of a mandrel which is used to insert the device into the stretched film.

Referring to FIG. 7, device 20 is mounted on another mandrel 80. Upper portion 82 and lower portion 86 of mandrel 80 have the same outer diameters as upper portion 72 and lower portion 76 of pin 70. Upper portion 82 has a conical relief 84 to receive device 20. It also has a support pin 88 which keeps device 20 from compressing when it is inserted into the stretched film 32. End 28 of device 20 has been capped off with epoxy or another appropriate technique to form a smooth hemispherical cap. Band 26 of end 30 is installed on support pin 88, and support pin slides through inner band 33 and inside device 20 until it contacts band 24 at end 28. Pin 88 then supports end 28 and device 20 during insertion into stretched film 32. Upper portion 82 also has a circumferential cutting groove 90 for trimming stretched film 32 after device 20 has been installed in film 32.

Figure 8:
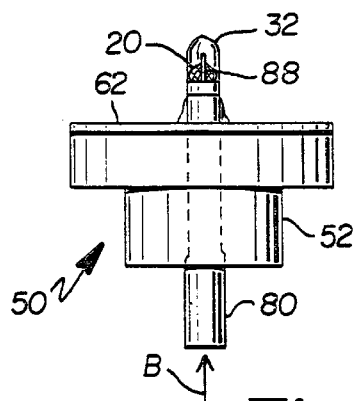
FIG. 8 is a side view of the mandrel of FIG. 7 being inserted into the holding fixture with stretched film of FIG. 6.

Referring to FIG. 8, mandrel 80 with device 20 attached is slid into holding fixture 50 in direction of arrow B and device 20 is pushed linearly into already stretched film 32.

Figure 9:
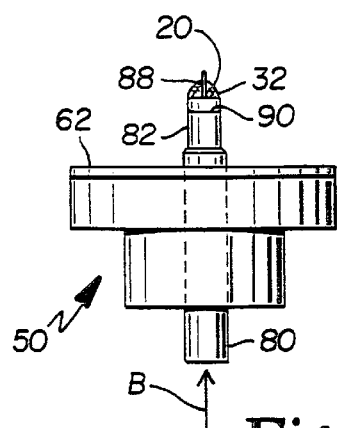
FIG. 9 is a side view of the holding fixture and mandrel of FIG. 8 showing the mandrel further inserted to stretch the film tight over the vascular occlusion device.

Referring to FIG. 9, after device 20 contacts stretched film 32, mandrel 80 is further advanced in the direction of arrow B which further stretches film 32 tightly over end 32 of device 20, the exposed surface of device 20, and upper portion 82. Insertion of mandrel 80 stops when film 32 has been stretched so that the area in which it is tight against upper portion 82 extends below cutting groove 90.

Figure 10:
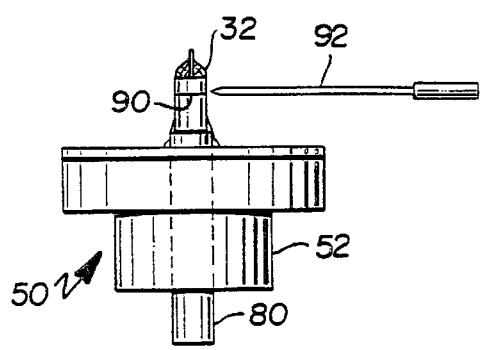
FIG. 10 is a side view of the assembly of FIG. 9 illustrating how the stretched film is cut.

Referring to FIG. 10, film 32 is cut circumferentially in cutting groove 90 using a razor blade 92 or other suitable cutting technique.

Figure 11:
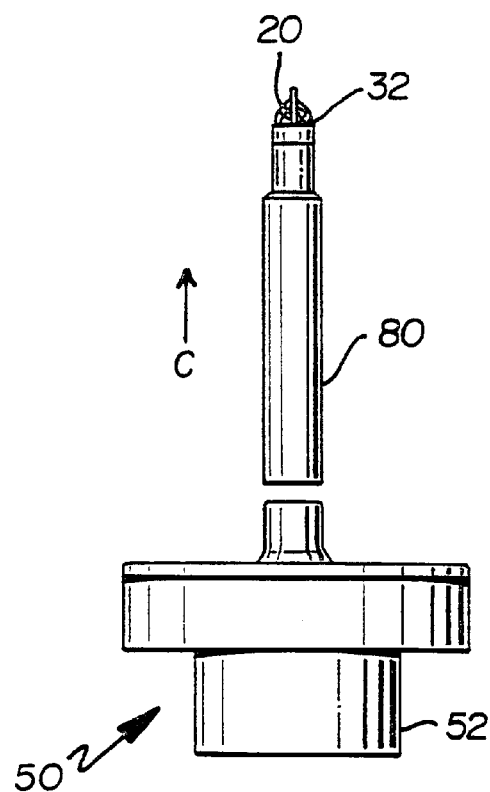
FIG. 11 is a side view of the holding fixture and mandrel showing the mandrel and the covered vascular occlusion device being removed from the holding fixture.

Referring to FIG. 11, mandrel 80 with device 20 now covered with film 32, is pushed through holding fire 50 in the direction of arrow C.

Figure 12:
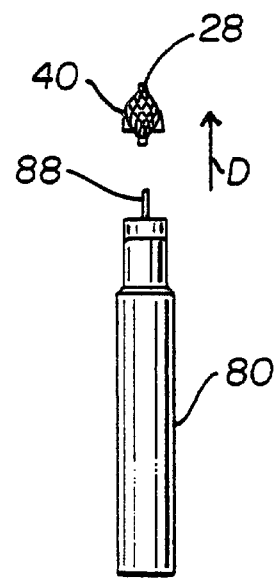
FIG. 12 is a side view of the mandrel showing the covered device being removed from the mandrel.

Referring to FIG. 12, the completed covered device 40 is then removed from mandrel 80 by grasping end 28 of device 40 and pulling it in the direction of arrow D to slide the covered device 40 off of support pin 88.

The preferred material for film 32 is low density polyethylene. Alternatively, film 32 could be made from a bioresorbable material such as polylactic acid or polyglycolic acid. Film 32 can be surface modified to impart a number of characteristics to its surface. Examples of such characteristics are increased lubricity (which may facilitate easier passage through the catheter), and increased surface energy (which may facilitate platelet activation on the surface of the film). Film 32 may also have a bioactive surface imparted on it by coating it with substances such as prothrombin and fibrinogen, both of which aid in organized clot formation. Film 32 could also be coated with a radiopaque material making device 40 easier to see under radiographic viewing.

In the preferred method described above for making covered device 40, film 32 is held on the device by mechanical interdigitation of film 32 and end 28 of the device 20. When the film 32 is wet, it also has an adhesive characteristic which holds it to wires 22. Alternatively, film 32 could be glued, welded, or melted onto end 28 to better secure it on device 20. Film 32 could also be tack welded over a number of wires 22 to secure it to the braided structure of wires 22.

Devices of other configurations such as those disclosed in the '110 application may also be covered with a film using the technique set forth above. Some devices may have to be partially stretched when installed in the film to facilitate optimal contact between the device and the film.

To use covered device 40, device 40 is installed on an introducer such as those disclosed in U.S. patent application entitled Introducer for an Expandable Vascular Occlusion Device mailed on MM/DD/98, which is a continuation in part of U.S. patent application Ser. No. 08/927,535 of the same title, mailed Sep. 8, 1997. The above patent application is hereby incorporated by reference. The introducer is used to introduce device 40 into a catheter for delivery to the intended site in a patient's vasculature.

Figure 13:
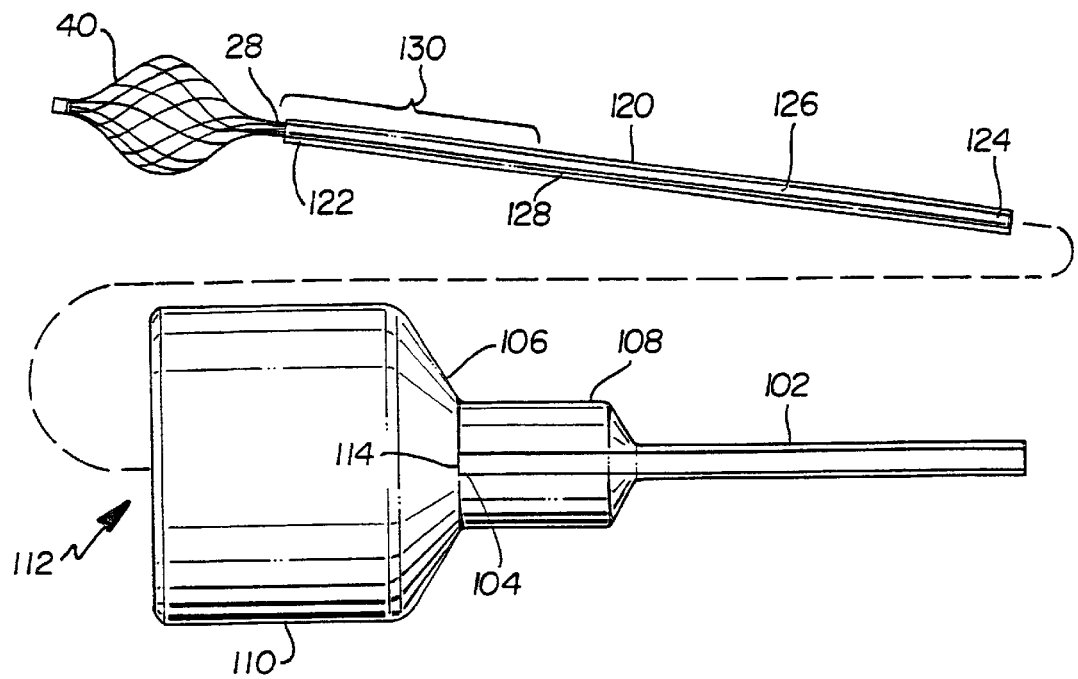
FIG. 13 is a side view of a vascular occlusion device and a partially disassembled introducer used to introduce the device into a catheter.
Figure 14:
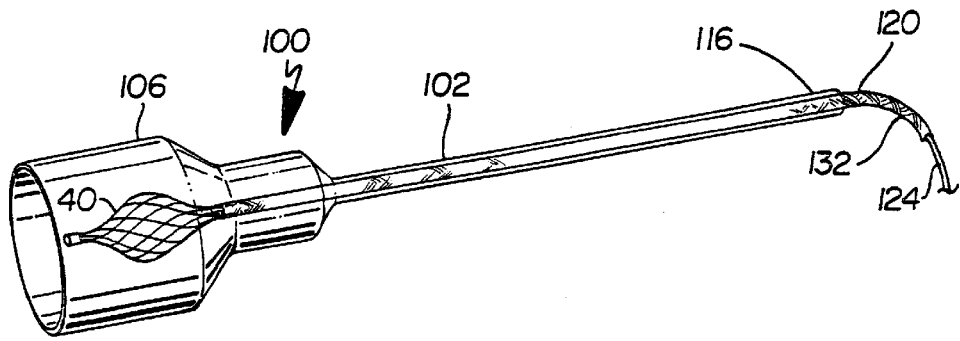
FIG. 14 is perspective view of an assembled introducer with a covered vascular occlusion device installed in it.

One embodiment of an introducer 100 suitable for use with covered device 40 is illustrated in FIGS. 13 and 14. The introducer 100 comprises an outer tube 102 and an inner member 120 sliding within an axial bore in the outer tube 102. The inner member 120 holds device 40 in a slotted tubular end of inner member 120, and positions device 40 at an end 114 of outer tube 102 and within a cup-shaped transparent shield member 106.

The outer tube 102 has a first end portion 104 on which is attached shield member 106. Shield member 106 preferably has a shank portion 108 with an internal bore which receives end portion 104 of outer tube 102. Shield member 106 also has cup portion 110 extending from shank portion 108. Cup portion 110 has an internal bore 112 large enough to receive device 40 with generous clearance around device 40. Outer tube 102 has a first end 114 which opens into bore 112 and preferably does not extend into bore 112.

Shield member 106 is preferably made of a transparent plastic material so that device 40 can be readily viewed on introducer 100. Shank portion 108 is affixed to outer tube 102 by methods such as gluing or welding, or shank portion 108 may simply have a friction fit on outer tube 102 and be pressed on it. Shield member 106 could also be molded directly onto tube 102, or shield member 106 and tube 102 could be molded as a single unit. Outer tube 102 may be a metal tube, a plastic tube, or an integrally molded extension of shank portion 108.

Inner member 120 is preferably a flexible plastic tube made of material such as polyethylene. Inner member 120 has a first end portion 122 of tubular configuration which has an axial slit allowing end 122 to expand radially to receive and grip end 28 of device 40.

Inner member 120 also may have a metal wire 126 disposed inside inner member 120. Metal wire 126 is coextensive with end 124 of inner member 120, and has an end 128 which terminates a significant distance from end 122 of inner member 120 leaving a portion 130 of inner member 120 unreinforced by wire 126. Metal wire 126 provides something solid for inner member 120 to cinch down against should the inner member 120 elongate and shrink diametrically under tensile load, thereby reducing recoil or "snapping" of inner member 120 as it is pulled through outer tube 102 to retract device 40 into outer tube 102.

To install a device 40 in the introducer 100 end 124 of inner member 120 is inserted into end 114 of outer tube 102 and pushed through outer tube 102 until end 124 of inner member 120 extends beyond end 116 of outer tube 102 and slit end 122 of inner member 120 extends an inch or so beyond shield member 106. End 28 of device 40 is installed in the slit end 122 of inner member 120, then end 124 is pulled to slide collet tube 120 further through outer tube 102 and pull device 40 inside of cup portion 110 of shield member 106. When the end 122 of inner member 120 gripping the device 40 enters the end 114 of outer tube 102, the grip of the end 122 of inner member 120 on end 28 of device 40 is tightened by compressive loading of end 122 of inner member 120. Sliding of inner member 120 is then stopped. End 124 of 120 is then bent to form a hook 132 at end 116 of outer tube 102. The hook 132 serves as a handle for grasping inner member 120 to retract device 40 into outer tube 102, and also functions to prevent the inner member 120 from sliding back toward the shield member and releasing device 40.

Device 40 is held by introducer 100 in its relaxed condition outside of the outer tube 102 prior to use. To use the device and the introducer; the hook 132 of the inner member 120 is grasped and pulled relative to outer tube 102 which pulls device 40 into outer tube 102 stretching device 40 to its cylindrical shape as it does so. Continued sliding of the inner member 120 moves the device 40 along the outer tube 102. When the end 122 of the inner member exits end 116 of the outer tube, the inner member 120 releases the device 40 such that most of the device remains in its stretched condition disposed inside the outer tube 102 at end 116. Inner member 120 is discarded and end 116 of outer tube is installed in catheter. A push rod or guidewire is then inserted into end 114 of outer tube 102 and advanced along tube 102 until it contacts device 40. The pushrod or guidewire is used to push the device in its stretched condition into the catheter and advance it through the catheter to the desired site of deployment. Shield member 106 provides a large diameter grasping member used for manually holding the introducer while manipulating the pushrod. When device 40 exits the catheter at the site of deployment, device 40 opens to its relaxed shape and lodges in a blood vessel. The film is pushed up against the vessel wall. Blood flow in that vessel is immediately and completely stopped when device 40 opens.

The preferable direction to install a covered vascular occlusion device, such as device 40, is such that the device exits the catheter in the same direction as the blood flow. In this direction, because end 30 is open, the arterial pressure wave pushes against the interior of the device and the film 32, thereby applying significant radial force to the vessel as it does so. That same arterial pressure also attempts to push the device 40 downstream. The force resisting this downstream movement is the frictional force generated by the device 40 pushing against the vessel wall. This frictional force is a function of the coefficient of friction between the film 32 and the vessel wall, the radial force, and the surface area of contact. The radial force is the total of the radial force generated by the wires 22 pushing against the vessel wall and systolic blood pressure pushing against the contact area of the film 32. The greater the contact area, the greater the frictional force.

Figure 15:
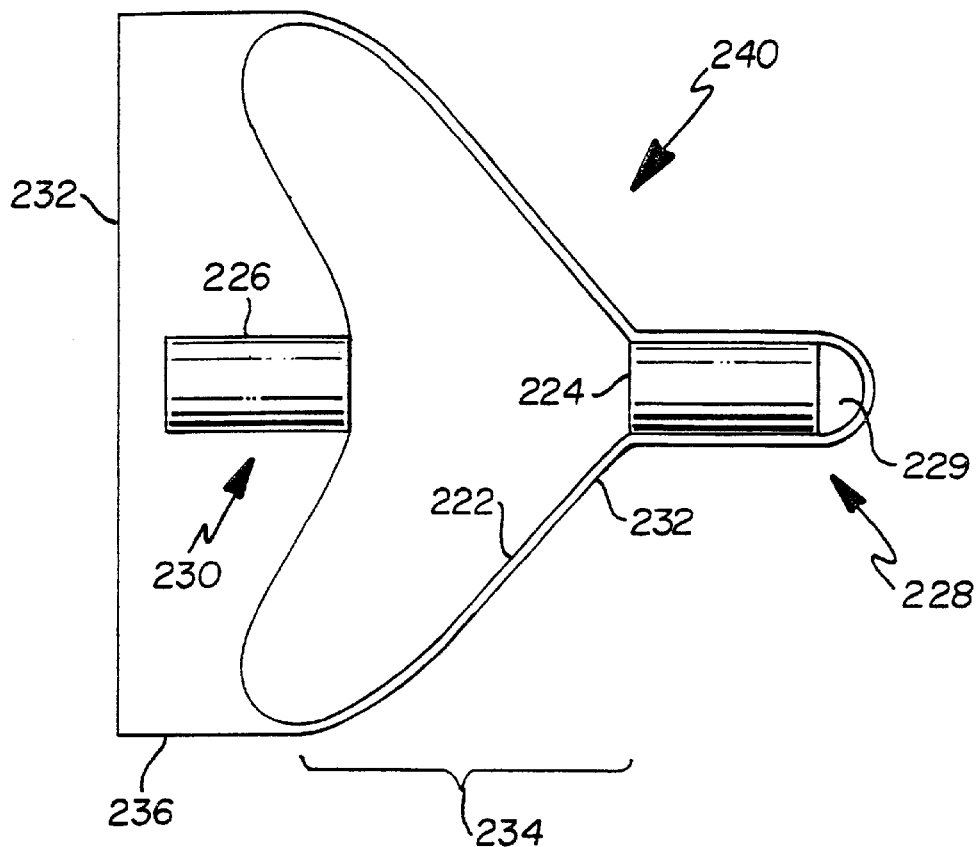
FIG. 15 is a side view of a conical shaped self-expanding vascular occlusion device with a film covering.

The above description has all been illustrated using the ball-like shape covered device 40. Another shape which can be formed from the same structure as the ball-like shaped device 40 is a conical-shaped device 240 illustrated in FIG. 15. Bands 224 and 226, wires 222, and hemispherical cap 229 are the same as those of device 40. To form device 240, end 230 is pushed closer to end 228 than in device 40, and wires 222 are shaped so that end 230 is invaginated. The device is heat set in is form. Portion 234 of device 240 then has a conical shape. Film 232 is installed on the conical shaped device as described above, and ski portion 236 of film 232 is trimmed so that skirt portion 236 extends beyond band 226. The conical shaped covered vascular occlusion device 240 is very useful for conical shaped vessels or vessels requiring a device which has greater radial force.

Figure 16:
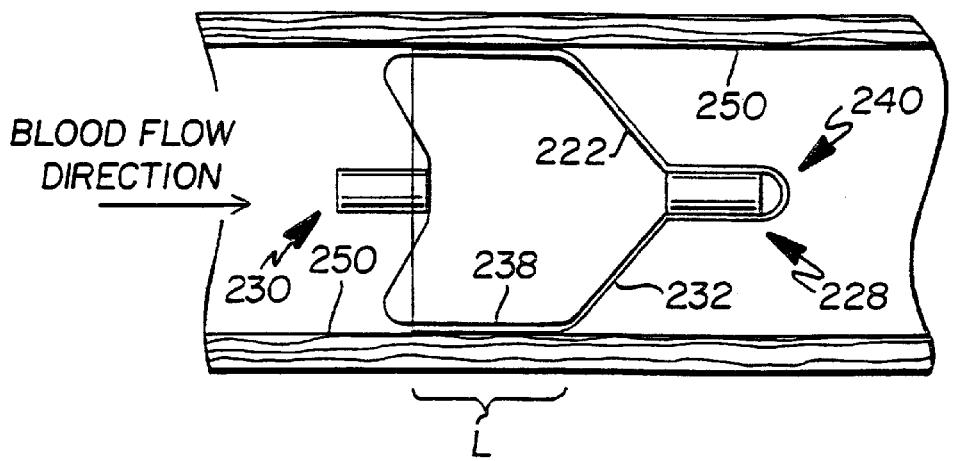
FIG. 16 is cross sectional view of the device of FIG. 15 installed in a blood vessel.

Referring to FIG. 16, if the conical device 240 is installed in a vessel of smaller diameter than its relaxed size, the device 240 cannot open to its original cone form. In that case, the outer portion 238 of wires 222 conform to vessel walls 250 over the length L, providing a larger contact area for film 232, which increases the radial force from the internal pressure due to the blood flow direction.

Referring to FIGS. 17 and 18, an alternative embodiment 300 of the vascular occlusion device is shown. One optional feature of this embodiment is melting a predetermined region 310 of the film 320 to the nitinol wires near the proximal band 330. This prevents migration of the film 320 distally when the device 300 is in an implanted position. FIG. 25 illustrates a method of melting the film 320 at the proximal end of the device 300. A support pin 360 used for passing the device into the film is relatively long. The film 320 is pulled tight around the distal tip of the device. Subsequently, the support 365 and the pin 370 are pushed, at the same time, pushing the device through a guide 375 having the same inner diameter as the introducer tube 380. As the device is pushed through the guide 375 there is an axially positioned tube 385, again having the same inner diameter as the introducer tube, on the other side of the guide 375 which keeps the device in its axially extended form. Once the proximal end of the device is beneath the region of the guide contain a heater 390, the heater 390 is turned on. The heater 390 melts the film 320 to the wires at this point. The excess film separates from the film on the device as the material contracts upon heating. The heater 390 is immediately turned off and the film is allowed to cool. Pin 370 is removed from the device, the tube 385 is retracted and the device is either pushed or pulled out of the tube 385.

Referring again to FIGS. 17 and 18, a second optional feature of this embodiment 300 is to cut, for example by heat, at least one hole 340 in the proximal side 350 of the device 300. Two or three holes may be cut instead of one. The hole 340 or holes allow blood to enter the device 300. This allows the device to open faster and to remain in place.

Referring to FIGS. 19–22, a further alternative embodiment of the vascular occlusion device is shown. This embodiment has particular utility in incontinence treatment. The device 400 includes tube 410 preferably constructed of polyethylene, distal and proximal bands 420a and b, respectively, a contact pad 430, a guidewire actuator, braiding, preferably constructed of nitinol, and a film disposed over the braiding, preferably constructed of polyethylene. The guidewire 440 disposed down the center of the device 400 and attached to band 420a and the tube 410 attached to the band 420b permits the device to be opened and closed for entry and retrieval, via actuation of the guidewire 440, into the urethra of both male and female patients, for example in the treatment of incontinence.

Referring to FIG. 23, another alternative embodiment of the vascular occlusion device is disclosed having the particular configuration or form shown.

Referring to FIG. 24, yet another alternative embodiment of the vascular occlusion device and an alternative method of making such embodiment, are disclosed. The device embodiment 600 includes a covering 610 comprising non-woven polymeric filaments. Such filaments may consist of, though not limited to, polyester or polyurethane. The process of constructing the device 600 comprises the step of spraying polymeric filaments 640, for example polyester or polyurethane, directly on to the braided, preferably nitinol, substructure 620 via one or more spray heads 630a and b, respectively, under conditions such that the filaments 640 stick to the nitinol substructure 620. The substructure 620 may be rotated during spraying.

The descriptions above and the accompanying drawings should be interpreted in the illustrative and not the limited sense. While the invention has been disclosed in connection with the preferred embodiment or embodiments thereof, it should be understood that there may be other embodiments which fall within the scope of the invention as defined by the following claims. Where a claim is expressed as a means or step for performing a specified function it is intended that such claim be construed to cover the corresponding structure, material, or acts described in the specification and equivalents thereof, including both structural equivalents and equivalent structures.

What is claimed is:

1. A method of making a covered vascular occlusion device, comprising the steps of:
   (a) providing the device with a braided wire member and at least first and second securing members affixed to the braided wire member at axially spaced locations, the first and second securing members being movable axially to shape a portion of the braided wire member intermediate the first and second securing members, the device being movable between a first stretched position in which the braided wire portion extends in an essentially cylindrical configuration to a maximum axial length and a minimum diameter, and a second relaxed position in which the axial length of the braided wire portion is reduced and its diameter is increased; and
   (b) spray coating polymeric filaments onto the braided wire member, under condition that the polymeric filaments stick to the braided wire member, for forming a film covering at least a portion of the device.

2. The method according to claim 1, wherein the polymeric filaments comprise non-woven polymeric filaments.

3. The method according to claim 1, wherein the polymeric filaments comprise polyurethane filaments.

4. The method according to claim 2, wherein the braided wire member comprises nitinol wires.

5. The method according to claim 1, further comprising the step of ($b_1$) rotating the braided wire member spraying the polymeric filaments.

* * * * *